(12) United States Patent
Ohmura

(10) Patent No.: US 6,923,794 B2
(45) Date of Patent: Aug. 2, 2005

(54) SKIN AND HAIR CARE APPARATUSES AND METHODS FOR PERFORMING SKIN CARE AND HAIR CARE

(75) Inventor: Shingo Ohmura, Hikone (JP)

(73) Assignee: Matsushita Electric Works, Ltd., Kadoma (JP)

( * ) Notice: Subject to any disclaimer, the term of this patent is extended or adjusted under 35 U.S.C. 154(b) by 189 days.

(21) Appl. No.: 10/236,948

(22) Filed: Sep. 9, 2002

(65) Prior Publication Data

US 2003/0055469 A1 Mar. 20, 2003

(30) Foreign Application Priority Data

Sep. 13, 2001 (JP) .................................. 2001-277907
Jan. 31, 2002 (JP) .................................. 2002-024627

(51) Int. Cl.[7] ................................................ A61F 7/00
(52) U.S. Cl. ..................................... 604/291; 392/385
(58) Field of Search ............................... 604/289–591; 34/96; 362/385; 239/136, 138

(56) References Cited

U.S. PATENT DOCUMENTS

| 3,745,306 | A | * | 7/1973 | Naritomi | .................. | 392/335 |
| 4,274,588 | A | * | 6/1981 | Schwob | .................... | 239/138 |
| 5,098,414 | A | * | 3/1992 | Walker | ...................... | 604/291 |
| 6,640,049 | B1 | * | 10/2003 | Lee et al. | ................... | 392/385 |
| 2003/0033726 | A1 | * | 2/2003 | Saida | ........................... | 34/96 |

FOREIGN PATENT DOCUMENTS

| DE | 730 363 | 1/1943 |
| GB | 1 284 761 | 8/1972 |
| JP | 62-38180 | 2/1987 |
| JP | 3046615 | 3/1998 |
| JP | 2000-356372 | 12/2000 |

* cited by examiner

Primary Examiner—Roy D. Gibson
(74) Attorney, Agent, or Firm—Oblon, Spivak, McClelland, Maier & Neustadt, P.C.

(57) ABSTRACT

A skin care apparatus includes a skin care unit and a negative ion supplying unit. The skin care unit is configured to perform skin care on a skin surface of human being. The negative ion supplying unit is configured to discharge negatively ionized air toward the skin surface and includes a negative ion generator which is configured to generate the negatively ionized air.

27 Claims, 15 Drawing Sheets

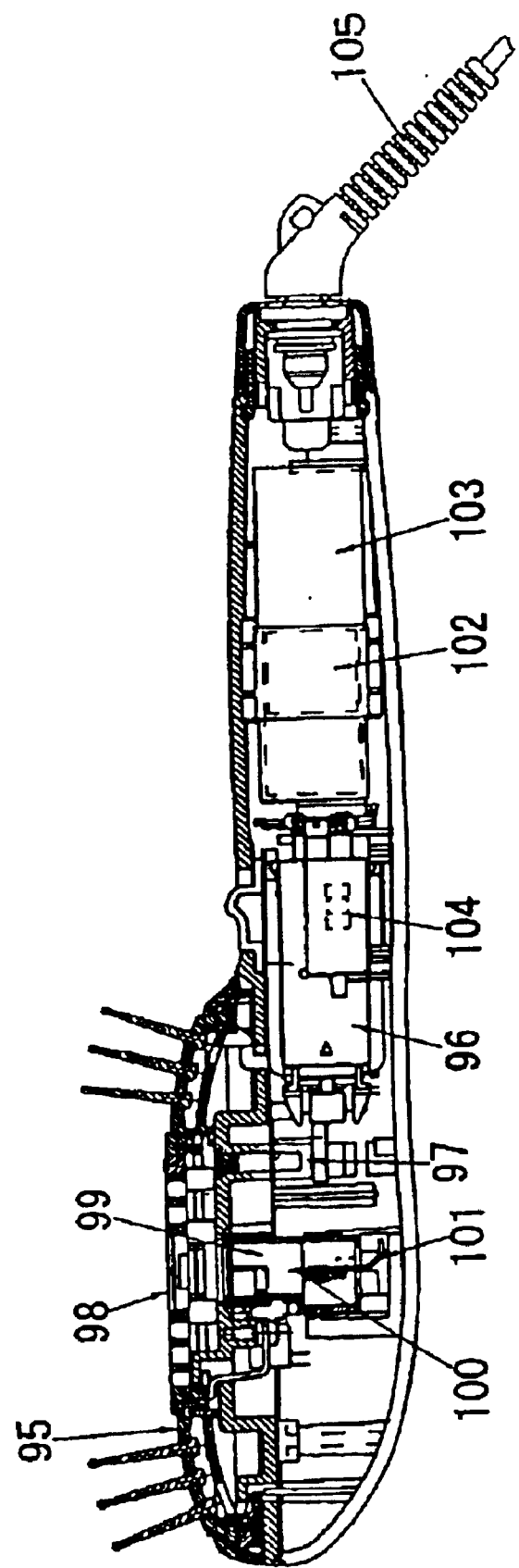

SKIN AND HAIR CARE APPARATUSES AND METHODS FOR PERFORMING SKIN CARE AND HAIR CARE

CROSS-REFERENCE TO RELATED APPLICATIONS

The present application claims priority to Japanese Patent Application No. 2001-277907, filed Sep. 13, 2001 and Japanese Patent Application No. 2002-024627, filed Jan. 31, 2002. The contents of these applications are incorporated herein by reference in their entirety.

BACKGROUND OF THE INVENTION

1. Field of the Invention

The present invention relates to a skin care apparatus and a hair care apparatus. The present invention further relates to a method for performing skin care and a method for performing hair care.

2. Discussion of the Background

As an example of conventional skin care apparatuses, a facial steam treatment apparatus (A) is structured, for example, as shown in FIG. 13. The apparatus includes a boiler 1 for storing water, a heater 2 which is connected to the boiler 1 in a sealed manner for heating and steaming water, a water supply cap 3 which is removably mounted to the boiler 1 in an airtight manner, a steam path 4 connected to the boiler 1 in an airtight manner, and a steam nozzle 5 which is connected the steam path 4 for discharging steam. Further, a heater 2, a steam on/off changeover switch 7, a high voltage electric discharging device 8 for making the steam in the steam path 4 to be fine particles, and a power cord 9 for power supply are connected to a control circuit 6. When facial steam treatment apparatus (A) is in use, the steam is discharged from the steam nozzle 5 after vaporized through heater 2, passed through steam path 4, and made into fine particles by high-pressure electric discharge device 8 so that the skin is treated by steam.

A treatment apparatus (B) is an example of the conventional hair care apparatuses, and structured as shown in FIG. 14. With this apparatus, an ion discharge outlet 11, from which negative ions are discharged, is provided on a surface of a bristle 10, and an ion nozzle 12 is provided in the ion discharge outlet 11. An ion electrode 13 is provided in the ion nozzle 12. The ion electrode 13 is connected to an ion generating circuit 15 via a high voltage lead wire 14. The ion generating circuit 15, an ion on/off changeover switch 17, and a power supply cord 18 for power supply are connected to the control circuit 16. Negative ions are discharged from an ion discharge outlet 1 when bristle 11 is used for combing or caring the hair.

As a conventional hair care apparatus, for example a hair dryer (C) is structured as shown in FIG. 15. The hair care apparatus has a suction inlet 19, a discharge outlet 20, a blowing fan 22, a motor 23, flow controlling wings 24 and a heater 25 in a cylindrical housing 21 which also functions as a handle part. Air discharge outlets 20 are formed on the surface of a bristle 26. Also, an ion outlet 27 for discharging negative ions are formed on the surface of a bristle 26. An ion nozzle 28 is provided in the ion outlet 27. An ion electrode 30 is provided in the ion nozzle 28. The ion electrode 30 is connected to an ion generating circuit 31 via a high voltage lead wire 29. And the ion generating circuit 31, the motor 23, the heater 25 and the power supply cord 33 are connected to an on/off changeover switch 32 which controls the operation of an air blow and ion discharge. While warm air is blown from the outlet 20 to dry hair, ions are discharged from the ion discharge outlet 27.

SUMMARY OF THE INVENTION

According to one aspect of the present invention, a skin care apparatus includes a skin care unit and a negative ion supplying unit. The skin care unit is configured to perform skin care on a skin surface of human being. The negative ion supplying unit is configured to discharge negatively ionized air toward the skin surface and includes a negative ion generator which is configured to generate the negatively ionized air.

According to another aspect of the present invention, a hair care apparatus includes a heating unit and a negative ion supplying unit. The heating unit is configured to heat hair to arrange the hair. The negative ion supplying unit is configured to discharge negatively ionized air toward the hair and includes a negative ion generator which is configured to generate the negatively ionized air.

According to yet another aspect of the present invention, a hair care apparatus includes a bristle, an air supplying unit, a steam supplying unit, and a negative ion supplying unit. The air supplying unit has an air discharging outlet on a surface of the bristle and is configured to supply air from the air discharging outlet. The steam supplying unit has a steam discharging outlet on the surface of the bristle and is configured to supply steam from the steam discharging outlet. The negative ion supplying unit has a negative ion discharging outlet on the surface of the bristle and is configured to supply negatively ionized air from the negative ion discharging outlet.

According to the other aspect of the present invention, a method for performing skin care includes treating skin surface of human being, and discharging negatively ionized air toward the skin surface.

According to the other aspect of the present invention, a method for performing hair care includes heating hair to arrange the hair, and discharging negatively ionized air toward the hair.

According to the further aspect of the present invention, a method for performing hair care includes supplying air from an air discharging outlet which is formed on a surface of a bristle, supplying steam from a steam discharging outlet which is formed on the surface of the bristle, and supplying negatively ionized air from a negative ion discharging outlet which is formed on the surface of the bristle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7 is a sectional view of a skin care apparatus according to another embodiment of the present invention;

DESCRIPTION OF THE EMBODIMENTS

Figure 1:
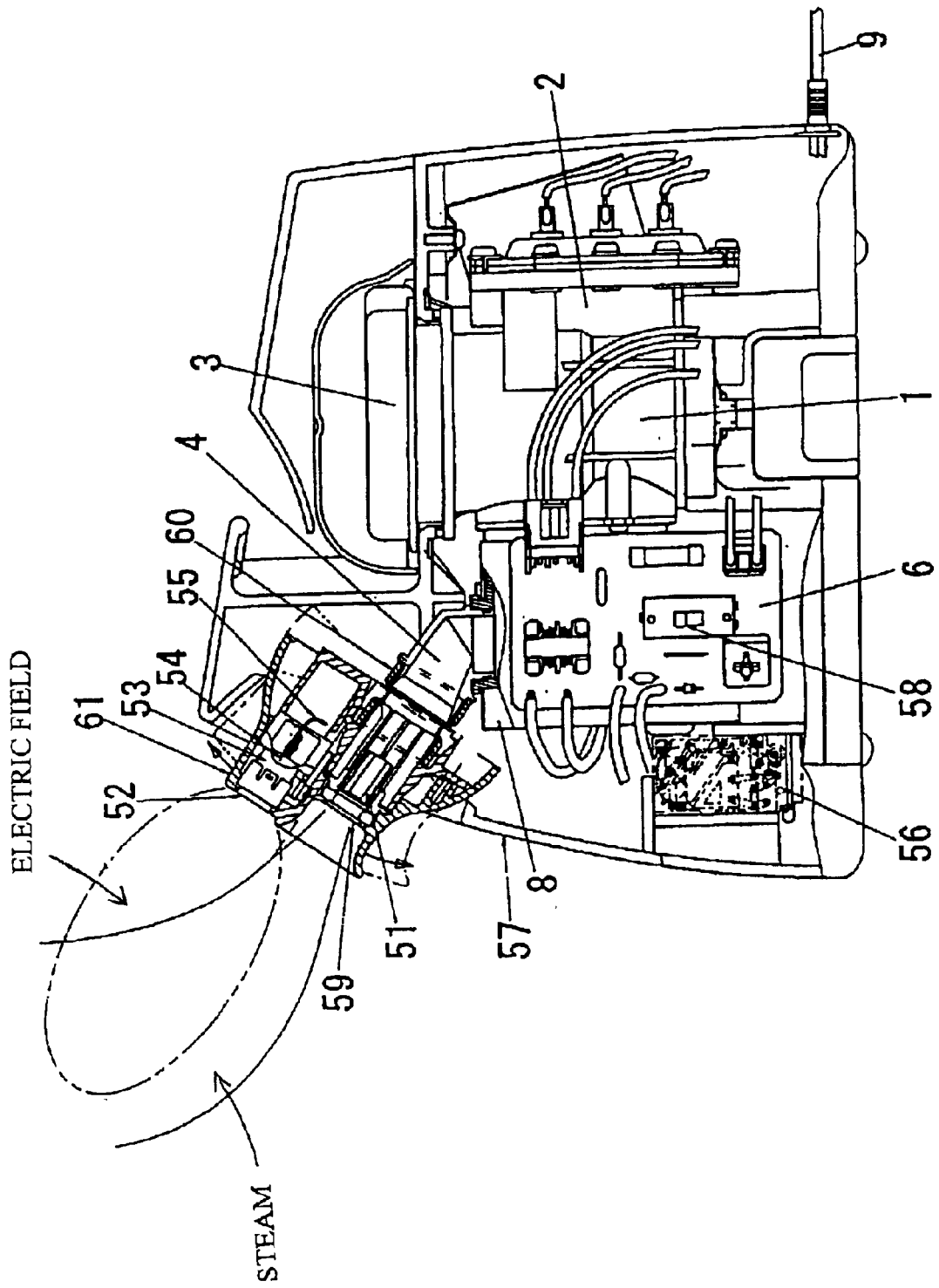
FIG. 1 is a sectional view of a skin care apparatus according to an embodiment of the present invention.

The embodiments will now be described with reference to the accompanying drawings, wherein like reference numerals designate corresponding or identical elements throughout the various drawings.

Figure 2A:
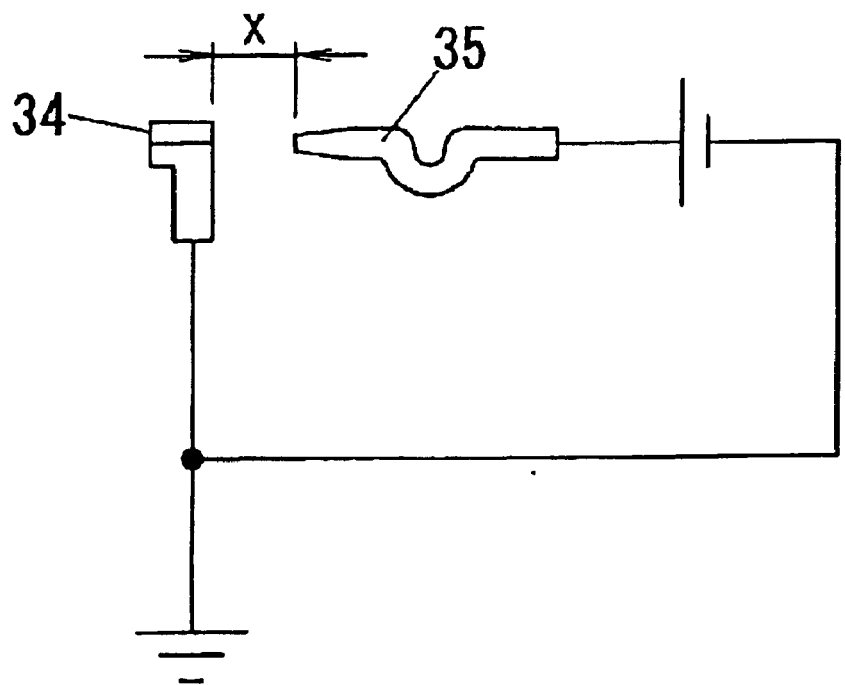
FIGS. 2(*a*) and 2(*b*) are schematic diagrams showing one example of a structure of a negative ion generator.
Figure 2B:
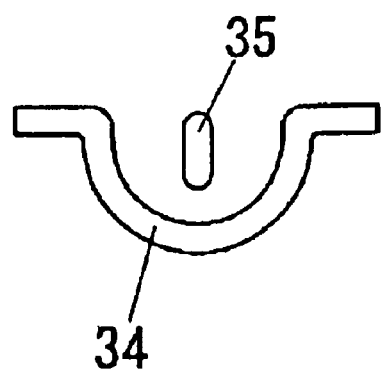

FIGS. 2(a) and 2(b) are schematic views showing a negative ion generator. The negative ion generator is, for example, an electric discharge type negative ion generator which uses corona discharge. Referring to FIGS. 2(a) and 2(b), a plate electrode 34 (for example SUS304) is provided to face a needle-shaped ion electrode 35 to which high voltage is applied. The distance "x" between the plate electrode 34 and the needle-shaped ion electrode 35 is determined to generate maximum amount of negatively ionized air. Experiment results show that the more negatively ionized air is generated when the plate electrode 34 is formed to semi-circular cylindrical shape. But it is not necessary to form the plate electrode 34 in a half cylindrical shape.

The skin care apparatus according to an embodiment of the present invention is configured to discharge negatively ionized air generated by the above mentioned negative ion generator. FIG. 1 is a schematic sectional side view of the facial steam treatment apparatus structured to discharge steam and negatively ionized air onto skin. Inside a housing 57, which is placed on a table or others, a steam generating device or a steam unit is provided. As a steam generating device, a boiler 1 holds water, which is heated and vaporized by a heater 2. A freely removal water supply cover 3 is placed on the boiler 1. Steam generated through the steam generating device is supplied to a steam nozzle 51 via a steam path 4 and discharged from a steam nozzle 51. The heater 2, a changeover switch 58, a high voltage electric discharging device 8 to make steam passing through the steam path 4 into fine particles and a power cord 9 for power supply are connected to a control circuit 6. The control circuit 6 also has such functions as steam generating status control and temperature control of the steam generating device.

The steam nozzle 51 for discharging steam is mounted on the exterior of the housing 57, and an ion nozzle 53 for discharging negatively ionized air is installed next to the steam nozzle 51. An ion discharge outlet 52 is built as an integrated part of the steam nozzle 51, and the ion nozzle 53 is connected to the ion discharge outlet 52. A high voltage lead wire 55 to be connected to the ion electrode 54, which is housed inside the ion nozzle 53, is connected to an ion generating circuit 56, and the ion generating circuit 56 is connected to a control circuit 6. Negatively ionized air generated by the negative ion generating device, which includes the ion electrode 54, the ion generating circuit 56 and others, is discharged from the ion discharge outlet 52 via the ion nozzle 53. The ion discharge outlet 52 is located to be vertically upper position of a steam discharge outlet 59 of the steam nozzle 51 and forward in the discharge direction of the steam and the negatively ionized air with respect to the steam discharge outlet 59. A joint 60 linking the steam nozzle 51 to a steam path 4 is made of elastic material (for example silicon rubber) so that the angles (protruding direction) of the steam nozzle 51 and a nozzle body 61 of the ion nozzle 53 are freely adjusted by bending the joint 60. A changeover switch 58 connected to the control circuit 6 is configured to turn on or off the operations of steam, fine particle steam and negatively ionized air.

While the facial steam treatment apparatus is in use, steam vaporized by the heater 2 passes through the steam path 4, is changed into fine particles by the high voltage electric discharge apparatus 8 if necessary, and spouts from the steam nozzle 51 and the steam discharge outlet 59. Thus the steam hits on the skin to perform the skin care. Negatively ionized air generated by the negative ion generating device is discharged from the ion discharge outlet 52 via the ion nozzle 53. When taking care of the skin in this way, negatively ionized air generated by negative ion generating device adheres to the skin, the moisture retention effect of skin is improved, and a moist and smooth skin surface is obtained. In addition to facial treatment effect of this facial steam treatment apparatus, since the a moist and smooth skin surface is obtained, the feeling becomes more desirable after the skin care treatment. Also negatively ionized air is discharged with steam, steam becomes negatively charged by negatively ionized air. This improves steam adherence, and the skin is activated by heat of steam which stimulates blood circulation of skin surface of the subjected area, resulting in effective moisture adhesion on the skin surface. As mentioned above, by placing the steam nozzle 51 and the ion nozzle 52 side by side and by discharging steam and negatively ionized air in substantially the same direction, steam is effectively charged with negatively ionized air.

Because the steam nozzle 51 and the ion nozzle 53 are integrated, and a projecting direction of the steam nozzle 51 and the ion nozzle 53 from housing 57 is freely adjustable, steam and negative ion discharge direction is adjusted to suite to the treated area. Accordingly, handling the nozzles is also improved. By arranging the ion nozzle 53 above the steam nozzle 51, steam is effectively charged with negatively ionized air by utilizing distributing electric field from the ion nozzle 53 because steam goes upward due to its characteristics. It is also desirable to arrange the ion discharge outlet 52 of the ion nozzle forward in the discharge direction with respect to the steam discharge outlet 59 of steam nozzle 51. Namely, since negatively ionized air is affected by humidity, an generating amount of the negatively ionized air reduces under high humidity. Thus, by arranging the ion discharge outlet 51 of the ion nozzle 53 forward in the discharge direction with respect to the steam discharge outlet 59 of the steam nozzle 51, the ion discharge outlet does not directly get in contact with steam, resulting no drops of negatively ionized air amount as well as stable discharge of ions, and thus effective charging of steam with negatively ionized air possible. In addition, since high voltage electric discharge device 8 which charges steam with negatively ionized air is provided to make steam into fine particles. The fine particles of the steam charged with negatively ionized air are easily absorbed into the skin. Since steam is made into fine particles, thermal capacity of the steam particle is small, eliminating uncomfortable feeling such as wettness and the like when steam particles get in contact with the skin.

The negatively ionized air and the steam may be simultaneously discharged, or only the negatively ionized air may be discharged without discharging the steam.

Figure 3:
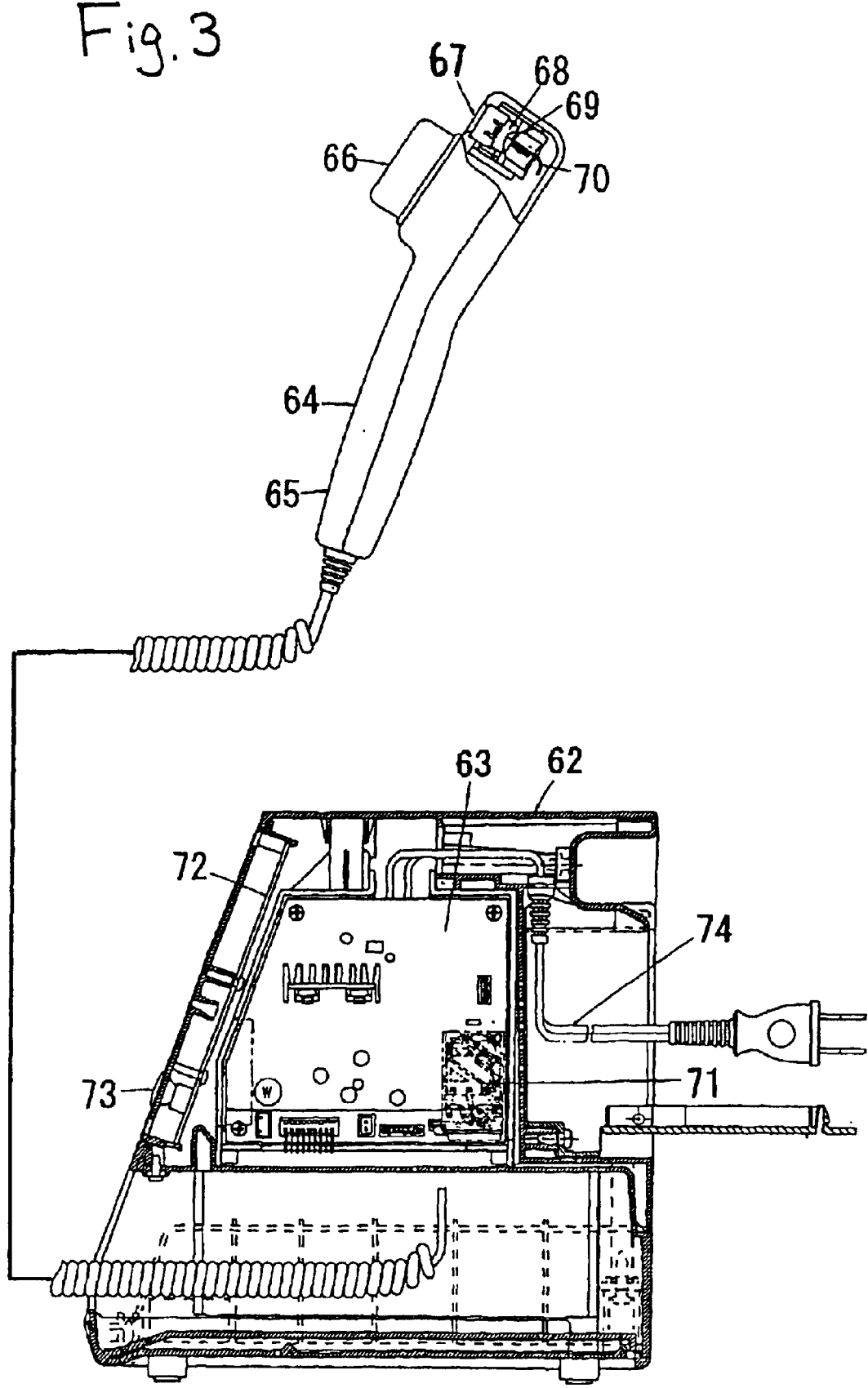
FIG. 3 is a sectional view of a skin care apparatus according to another embodiment of the present invention.

FIG. 3 shows another example of a skin care apparatus in which an ultrasonic facial care apparatus discharges negatively ionized air. The apparatus includes an ultrasonic generating circuit 63 inside a body 62, a probe 64 which is connected to the ultrasonic generating circuit 63. The probe 64 includes a hand holder 65, a contact element 66 and an ion discharge outlet 67. An ion nozzle 68 is connected to the ion discharge outlet 67. The ion nozzle 68 includes an ion electrode 69 which is connected to an ion generating circuit 71 via a high voltage lead wire 70. Negatively ionized air generated by the negative ion generating device which includes an ion electrode 69 and an ion generating circuit 71 is discharged from the ion discharge outlet 67 via the ion nozzle 68. The ion generating circuit 71, the ultrasonic generating circuit 63, a changeover switch 73 to turn on or off ultrasonic and negative ion operations, and a power cord 74 for power supply are connected to a control circuit 72.

This ultrasonic system facial treatment apparatus is used by holding the probe 64 with a hand and contacting the contact element 66 with face. The contact element 66 when in use vibrates by ultrasonic to stimulate the skin to perform skin care. In addition, negatively ionized air generated by the negative ion generator is discharged from the ion discharge outlet 67. Through these procedures, negatively ionized air generated by the negative ion generator adheres to the skin to improve moisture retention, and moist and smooth skin surface touch is obtained. Since the moist and smooth skin surface touch is added to skin care effect by stimulation of ultrasonic vibrations of this ultrasonic wave system facial treatment apparatus, touch of feeling becomes more desired after skin care.

Figure 4:
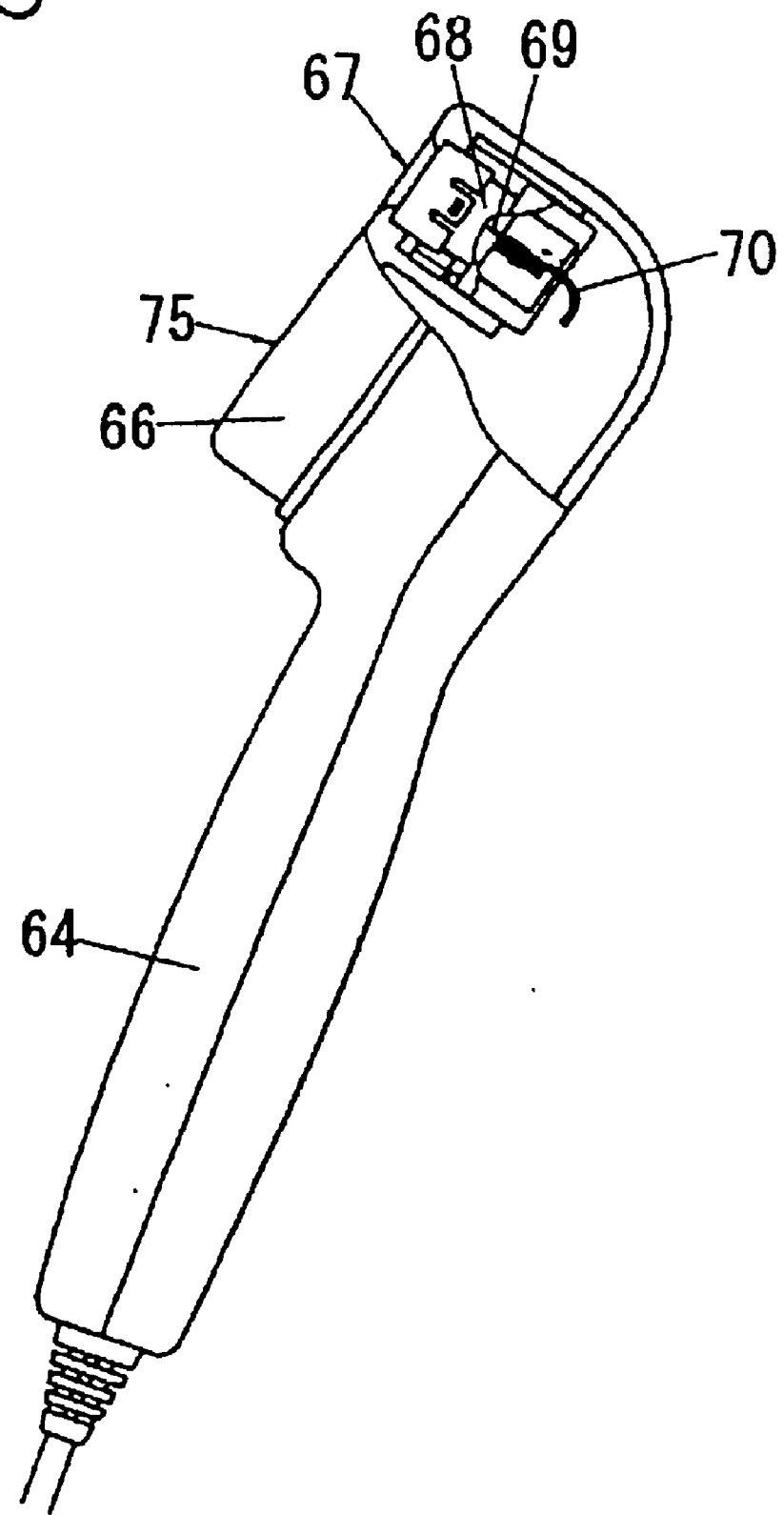
FIG. 4 is an enlarged partially cross-sectional view of a part shown in FIG. 3.

Referring to FIG. 4, with the above mentioned ultrasonic facial treatment apparatus, it is better to have the ion discharge outlet 67 at a skin contact surface 75 of the contact element 66 of the probe 64. When the ion discharge outlet 67 is open at the skin contact surface 75 of the contact element 66, the ion discharge outlet 67 of the contact element 66 is constantly in contact with skin. Therefore, more negatively ionized air is securely adhered to the skin.

Figure 5A:
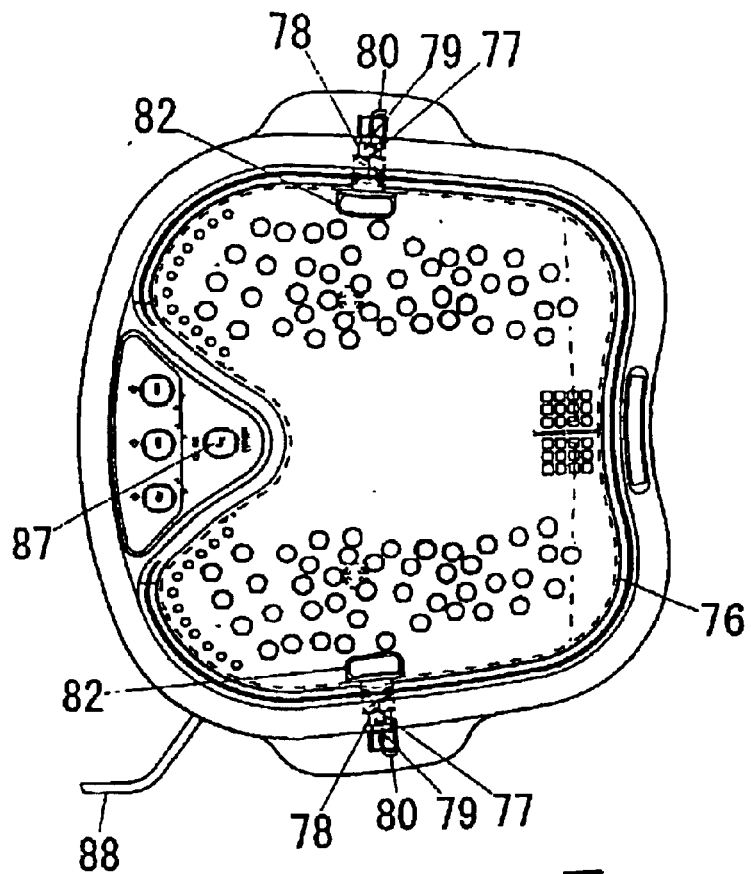
FIG. 5(*a*) is a top plan view of a skin care apparatus according to another embodiment of the present invention.
FIG. 5(b) is a sectional view of the skin care apparatus shown in FIG. 5(a)
Figure 5B:
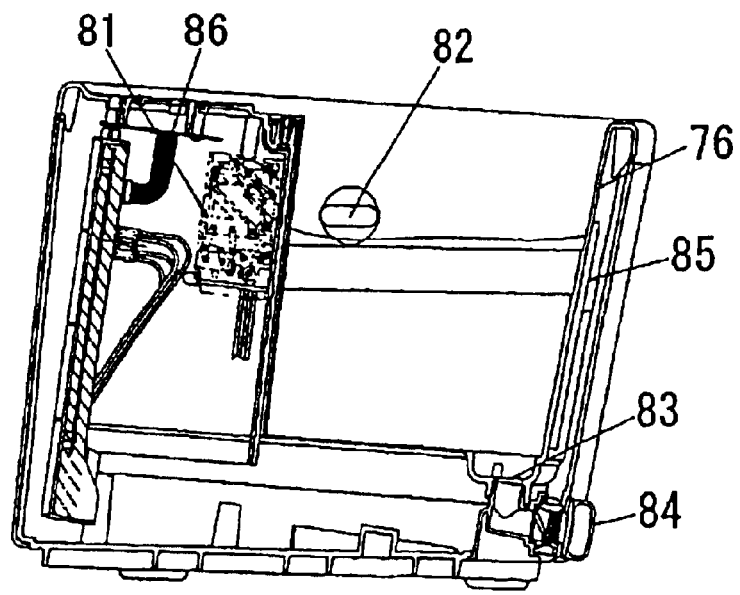

FIGS. 5(a) and 5(b) show another example of skin care apparatus, which is a foot bath having a negative ion discharge system. The apparatus includes a tank 76 which contains water. An ion discharge outlet 77 is formed on an inner wall surface of this tank 76, and connected to an ion nozzle 78. An ion electrode 79 housed in the ion nozzle 78 is connected to an ion generating circuit 81 via a high voltage lead wire 80. A freely removal cap 82 is placed at the ion discharge outlet 77. The cap 82 is provided during feet bath. After feet bath, the drain plug 84 is removed from the drain 83 which is formed at the bottom of the tank 76. After water is drained, the cap 82 is removed to discharge negatively ionized air. The volume of the tank 76 is designed to accommodate feet, and a heater 85 for warming up the water is provided at the exterior wall of the tank. The ion generating circuit 81, warming up heater 85, changeover switch 87 to turn on or off the operation of negatively ionized air and the heater, a power cord 88 for power supply are connected to the control circuit 86.

First drain 83 of tank 75 of feet bath is closed with the drain plug 84 and also the cap 82 is placed at the ion discharge outlet 77. Then, feet are put into the water in the tank 76. The warming up heater 85 is adjusted. When feet bathing is finished, the drain plug 84 is removed and water in the tank 75 is drained from the drain 83. Then the cap 82 is removed to open the ion discharge outlet 77. Accordingly, feet are exposed to negatively ionized air which is generated by the negative ion generator and discharged from ion discharge outlet 77. Moisture retention character and touch feeling effect of feet improve when first feet get enough water in the tank 76 filled with water and negatively ionized air is irradiated onto the feet. In addition, by using warm water in the tank 76 for bathing, blood circulation of feet are stimulated, and it is possible to keep feet in healthy state by eliminating swelling of feet, sensitivity to cold, and the like.

Figure 6A:
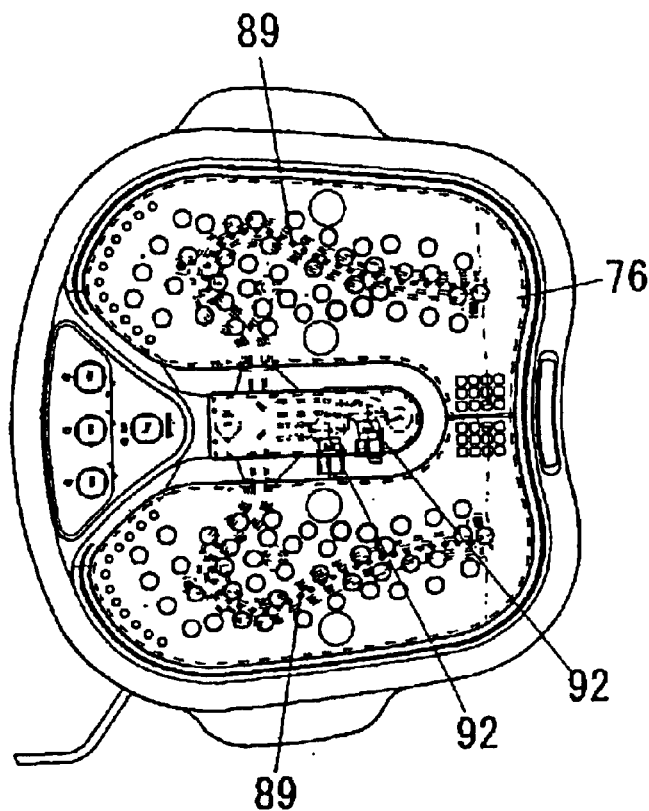
FIG. 6(a) is a top plan view of a skin care apparatus according to another embodiment of the present invention.
Figure 6B:
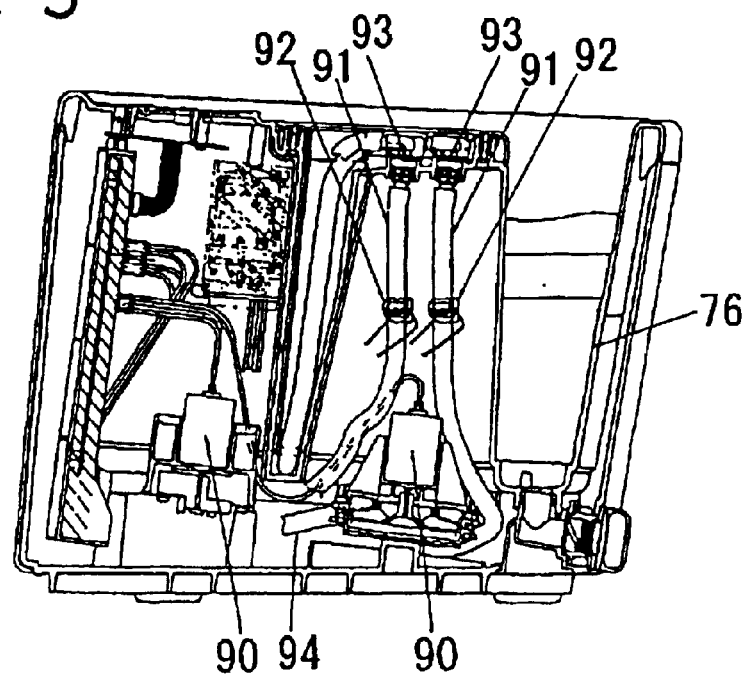
FIG. 6(b) is are sectional view of the skin care apparatus shown in FIG. 6(a)

FIGS. 6(a) and 6(b) show another example of a feet bath which discharges negatively ionized air. On the bottom plate of a tank 76, an air discharging outlet 89 is formed for discharging air while feet are in the bath, and an ion discharge outlet 92 is formed in an air discharging path 91 which connects air discharging outlet 89 and a pump 90. A check valve 93 is mounted between the air discharging outlet 89 and the ion discharge outlet 92 to prevent the water from flowing into the ion discharge outlet 92 and the pump 90. The ion discharge outlet 92 may be arranged at the pump suction side 94. In this case, the check valve 93 may be omitted by adding a mechanism to prevent water from flowing into the pump 90.

First water is supplied to the tank 76. Then, feet are soaked in the water. During the bathing, air bubbles come out from air discharging outlet 89 by driving the pump 90. Moreover, by discharging the negatively ionized air from the ion discharge outlet 92, air bubbles containing negatively ionized air may be supplied to the water. By this way, negatively ionized air is discharged as air bubbles into water in the tank 76 in an effective manner, it is possible to shorten the duration during which the skin care is performed because feet are receive negative ion effect while feet are soaked in the warm water.

FIG. 7 shows another example of a skin care apparatus, which is a head skin care apparatus discharging negatively ionized air. The apparatus includes a vibration generator 97 having a motor 96 to vibrate a bristle 95, and ion discharge outlet 98 formed on the bristle 95 to discharge negatively ionized air so as to stimulate head skin with vibrations. An ion nozzle 99 is connected to an ion discharge outlet 98. The ion nozzle 99 includes an ion electrode 100 which is connected to an ion generating circuit 102 via a high voltage lead wire 101. The motor 96, the ion generation circuit 102, a changeover switch 104 to control vibrations and negatively ionized air, and a power cord 104 for power supply are connected to a control circuits 103.

In this head skin care apparatus, head skin care is performed by giving stimulation to head skin with contacting vibrating bristle 95 onto head skin. In addition, by discharging negatively ionized air generated by the negative ion generator, negatively ionized air is irradiated onto head skin.

Since vibrations give massage effect onto head skin to promote blood circulation and to activate head skin while negatively ionized air is irradiated onto head skin, moisture retention and touch feeling effect improve. Thus, head skin may be made in healthy state.

Figure 8:
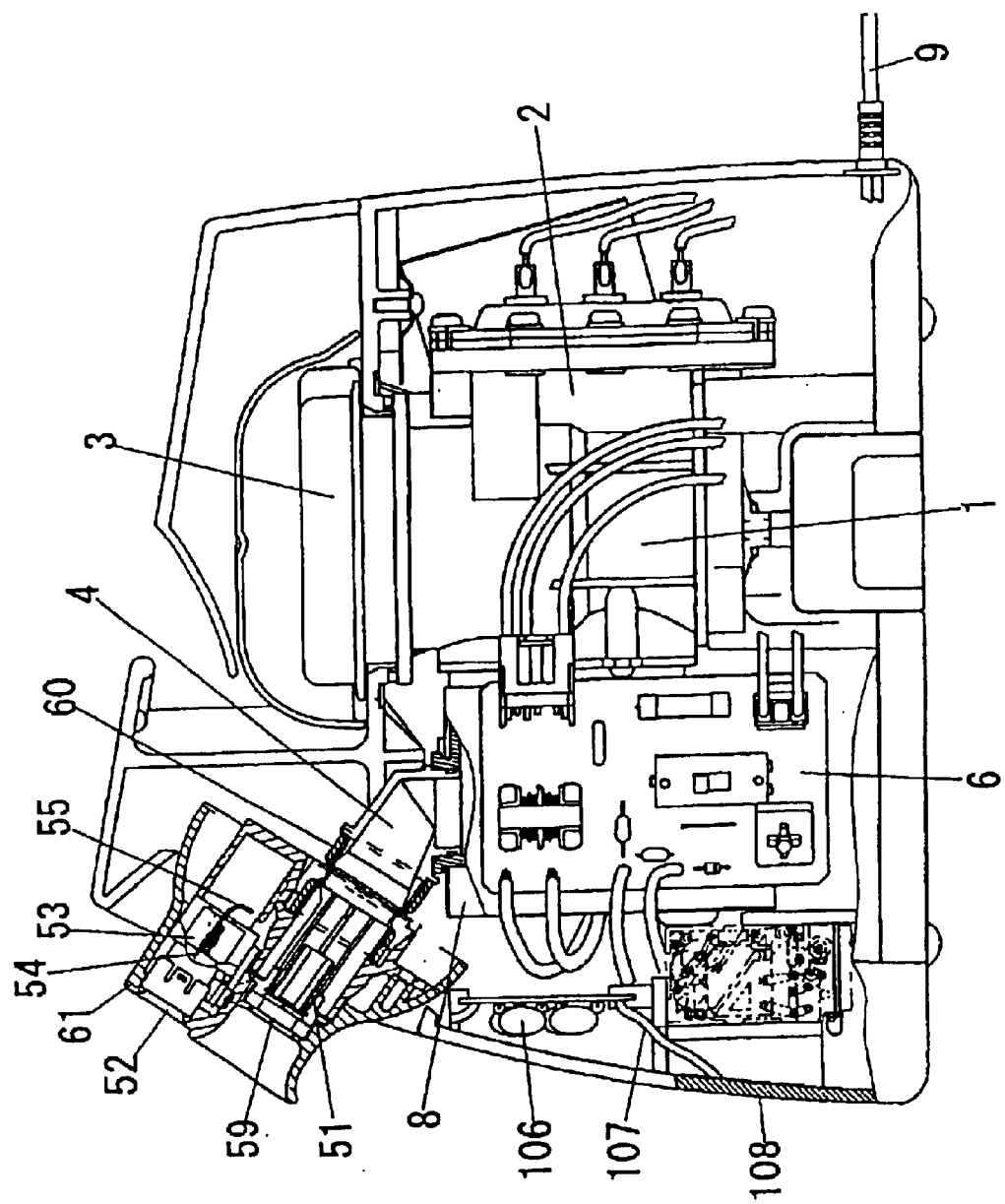
FIG. 8 is a sectional view of a skin care apparatus according to another embodiment of the present invention.

FIG. 8 shows another example of a skin care apparatus, which is a facial steam treatment apparatus equipped with a negative ion discharge part and an electric terminal. An electrical charge circuit 106 is connected to the control circuit 6. The electrical charge circuit 106 is further connected to an electric terminal 108 via a lead wire 107. The lead wire 107 is connected to the electric terminal 108, for example, with an aluminum tape or the like. It is desired to add anti-charged function to the electric terminal 108. For example, the electric terminal 108 is made of molded resign product containing electric charge prevention agent.

When this facial steam treatment apparatus is being used, steam evaporated by heater 2 passes through a steam path 4. The steam is made into fine particles by high voltage electric discharging device 8 if necessary. The steam is discharged from the steam discharge outlet 59 via the steam nozzle 51 to perform skin care. In addition, negatively ionized air generated by the negative ion generator is discharged from the ion discharge outlet 52 via the ion nozzle 53. By continuously touching the electric terminal 108 to the face while using the facial steam treatment apparatus, skin is maintained at positive electric potential. By keeping the body at positive electric potential, electric charge saturation of negative ion may be avoided. Thus, more negatively ionized air is attracted to positively charged skin, making ions easily adhere to the skin.

Figure 9:
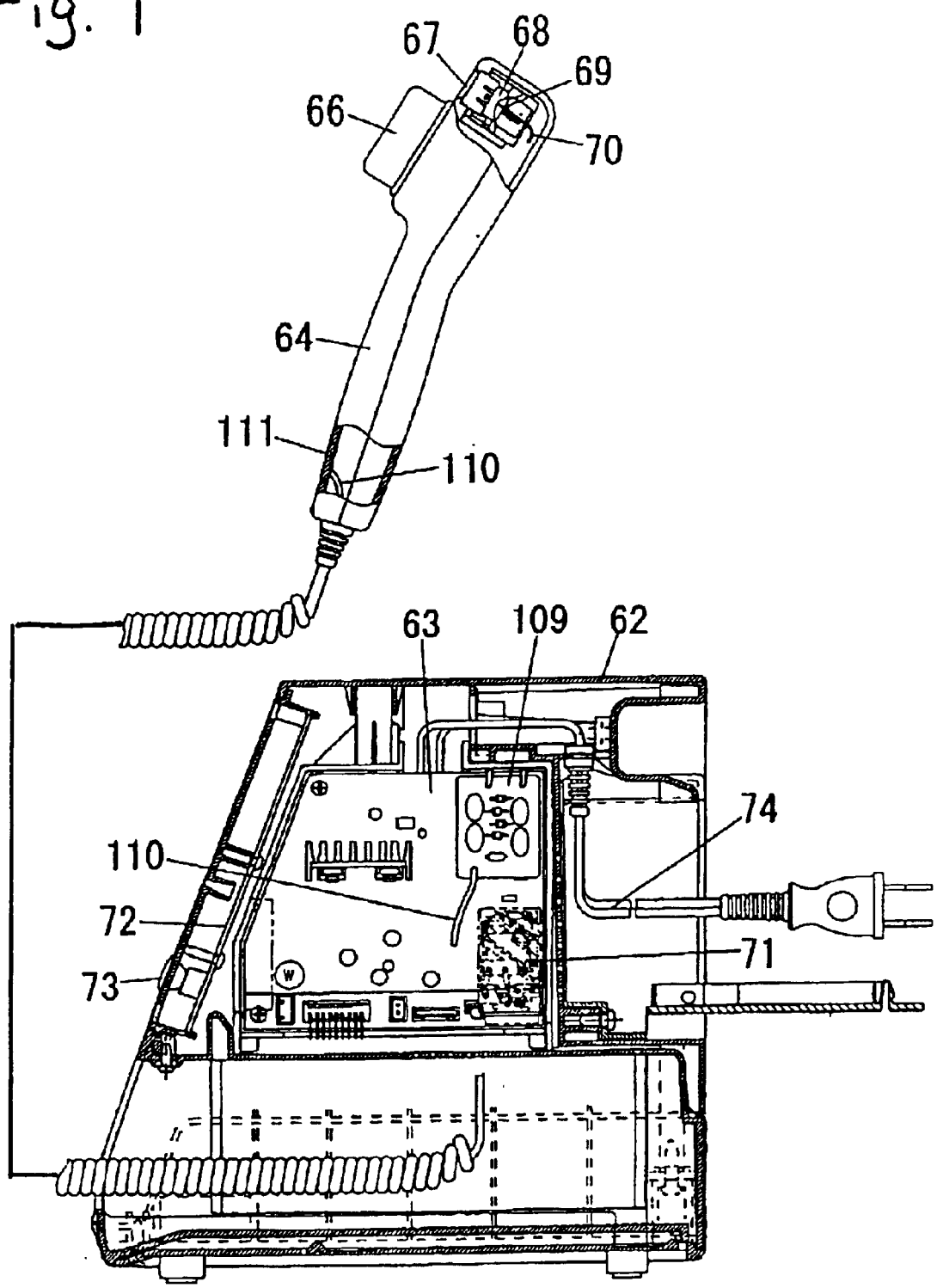
FIG. 9 is a sectional view of a skin care apparatus according to another embodiment of the present invention.

FIG. 9 shows other example of a skin care apparatus, which is an ultrasonic facial treatment apparatus having a negative ion discharge part and an electric terminal. An electrical charge circuit 109 is connected to the control circuit 72. The electrical charge circuit 109 is further connected to a housing 111 via a lead wire 110. The lead wire 110 is connected to the housing 111, for example, with an aluminum tape or the like. It is desired to add anti-charged function to the housing 111. For example, the housing 111 is made of molded resign product containing electric charge prevention agent.

This ultrasonic facial treatment apparatus is used by holding the probe 64 with a hand and put the contact element 66 on face. The contact element 66, when in use, generates ultrasonic vibrations to stimulate the skin to perform skin care. In addition, negatively ionized air generated by the negative ion generator is discharged from the ion discharge outlet 67. Since the user touches the housing 11 by holding the probe 64 while using the ultrasonic facial treatment apparatus, the body of the user is maintained at positive electric potential. By keeping the body at positive electric potential, electric charge saturation of negative ion may be avoided. Thus, more negatively ionized air is attracted to positively charged skin, making ions easily adhere to the skin. When using the ultrasonic facial treatment apparatus, skin is maintained at positive electric potential.

Figure 10:
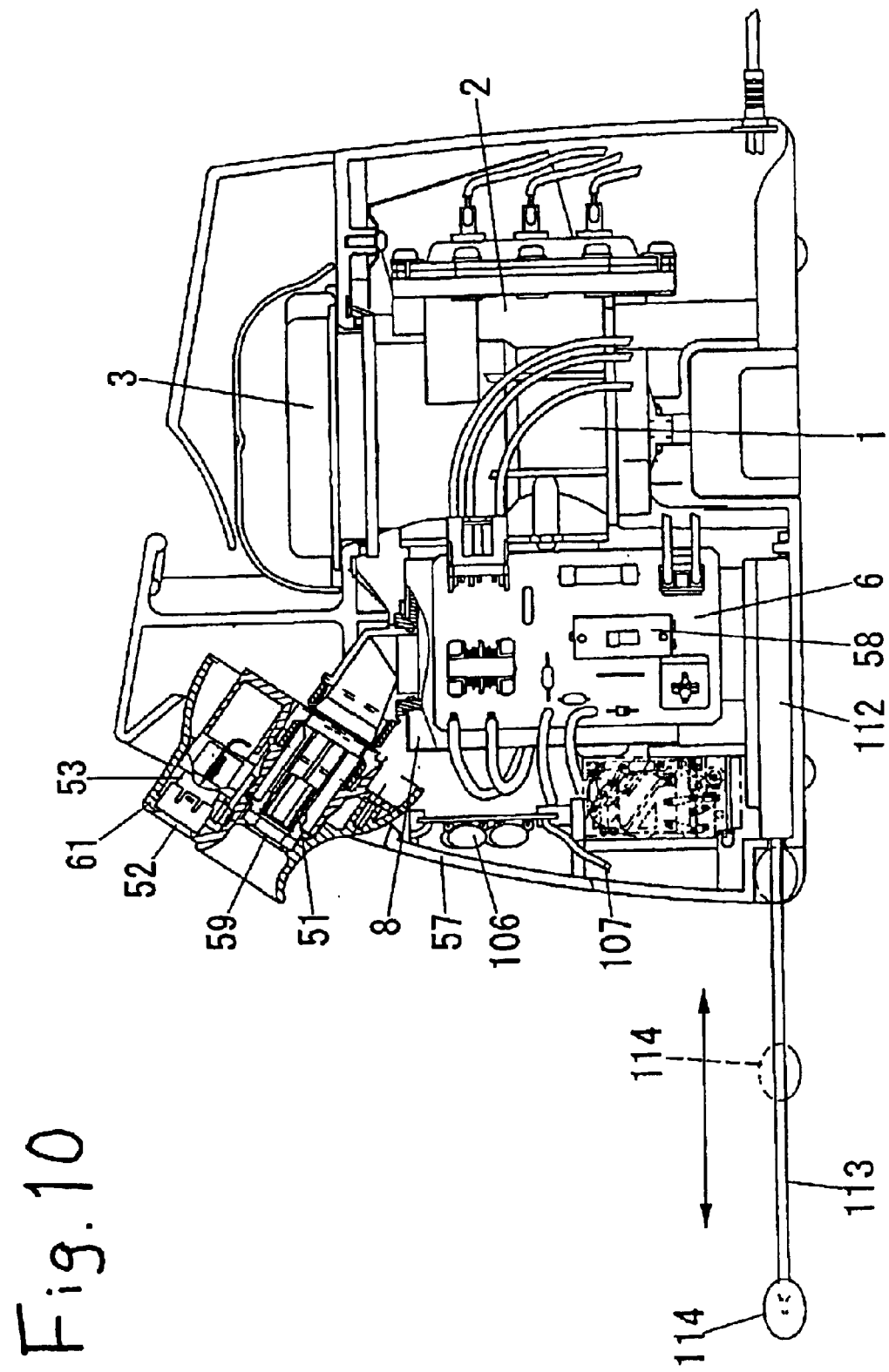
FIG. 10 is a sectional view of a skin care apparatus according to another embodiment of the present invention.

FIG. 10 shows another example of a skin care apparatus, which is a facial steam treatment apparatus having a negative ion discharge part and an electric terminal that is freely pulled out. An electrical charge circuit 106 is connected to the control circuit 6. The electrical charge circuit 106 is further connected to a wiring cord 113 which is housed in a cord length adjustment mechanism 112 via a lead wire 107. An electric terminal 114 is provided at the end of the wiring cord 113. At the electric terminal 114, the wiring cord 113 is completely molded. It is desired to add anti-charged function to the electric terminal 114. For example, the electric terminal 114 is made of molded resign product containing electric charge prevention agent.

When this facial steam treatment apparatus is used, steam evaporated by the heater 2 passes through the steam path 4. The steam is made into fine particles by high voltage electric discharging device 8 if necessary. The steam is discharged from the steam discharge outlet 59 via the steam nozzle 51 to perform skin care. In addition, negatively ionized air generated by the negative ion generator is discharged from the ion discharge outlet 52 via the ion nozzle 53. By continuosly touching the electric terminal 114 while using the facial steam treatment apparatus, skin is maintained at positive electric potential. By keeping the body at positive electric potential, electric charge saturation of negative ion may be avoided. Thus, more negatively ionized air is attracted to positively charged skin, making ions easily adhere to the skin. In the present embodiment, the user can touch the electric terminal 114 at a location apart from the apparatus body. Accordingly, it is possible to maintain safely the skin at the positive electric potential while using this facial steam treatment apparatus.

Figure 11:
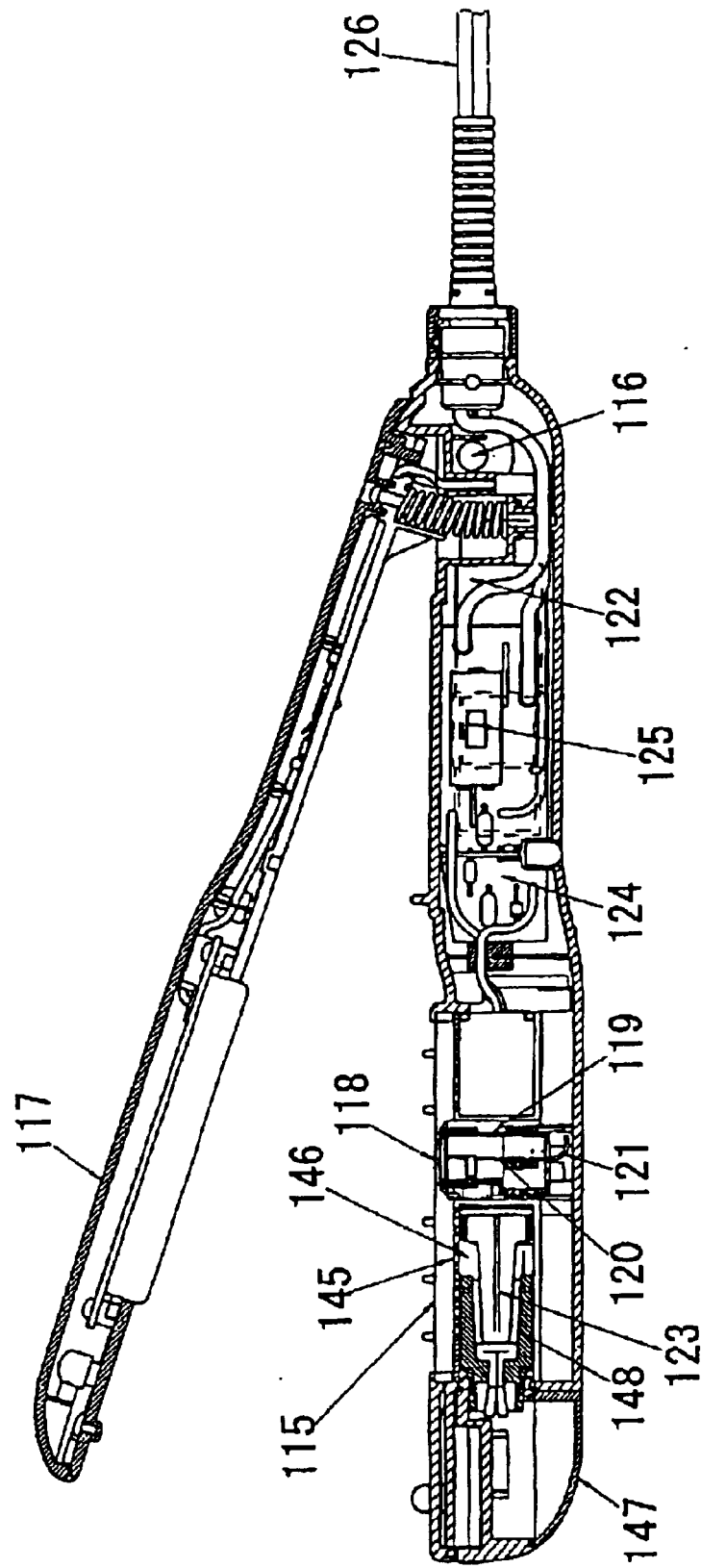
FIG. 11 is a sectional view of a hair care apparatus according to another embodiment of the present invention.

FIG. 11 shows an example of a hair care apparatus, which is a hair ironing apparatus having a hair heating maintenance mechanism, a steam discharge part, and negative ion discharge part. The apparatus includes a heating plate 115 equipped with a heater 123, a movable plate 117 movable around a movable fulcrum 116, a steam discharge outlet 145, and an ion discharge outlet 118. Hair is sandwiched between the heating plate 115 and the movable plate 117. An ion nozzle 119 is connected to the ion discharge outlet 118. The ion nozzle 119 includes an ion electrode 120 which is connected to an ion generating circuit 122 via a high voltage lead wire 121. Negatively ionized air generated by the negative ion generator, which includes the ion electrode 120 and the ion generating circuit 122, is discharged from the ion discharge outlet 118. The steam discharge outlet 145 is connected to a chamber 146 equipped with the heater 123. Water is supplied to the heater 123 from the removal tank 147 through capillary tubes provided in the felt 148. The heater 123, the ion-generating circuit 122, a changeover switch 125 to turn on or off the discharge of the negatively ionized air, and power cord 126 for power supply are connected to a control circuit 124. By changing the changeover switch 125, it is possible to turn on generating operation of negatively ionized air while the heater is on, or to turn on generating operation of negatively ionized air while the heater is off.

In this hair iron, hair is arranged by heating up the heating plate 115 by turning on the heater 123, and by holding hair between the heating plate 115 and the movable plate 117. Then, steam generated in the chamber 146 of the steam generating device is discharged from the steam discharge outlet 145 to the sandwiched and pressed hair between the heating plate 115 and the movable plate 117, and negatively ionized air generated by the negative ion generator is simultaneously discharged from the ion discharge outlet 118 to the hair held between the heating plate 115 and the movable plate 117. In this way, steam supplements the water lost from the hair through heating process. Furthermore, discharged negatively ionized air improves moisture retention and touch of the hair, feeling of the hair becomes more desirable after the hair care process.

Figure 12A:
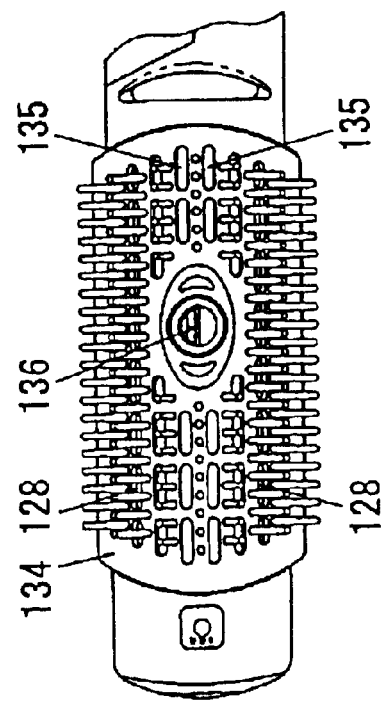
FIG. 12(a) is a top plan view of a hair care apparatus according to another embodiment of the present invention.
Figure 12B:
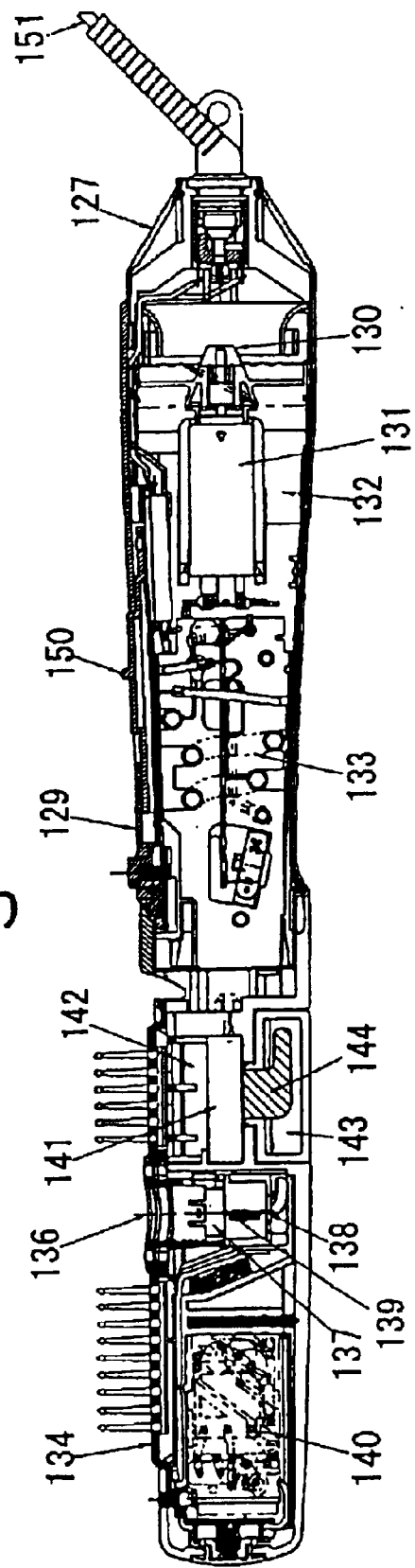
FIG. 12(b) is a sectional view of the hair care apparatus shown in FIG. 12(a)
Figure 13:
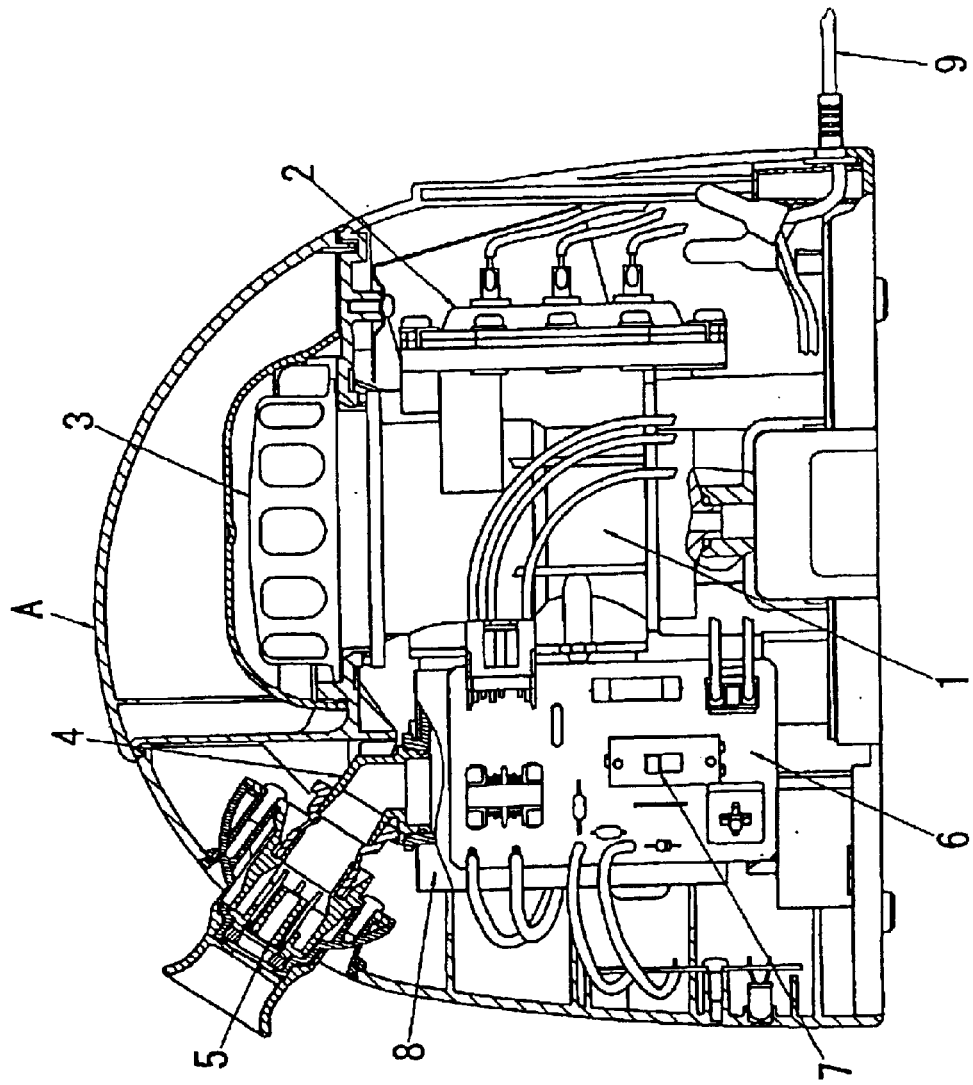
FIG. 13 is a sectional view of a conventional facial steam treatment apparatus.
Figure 14:
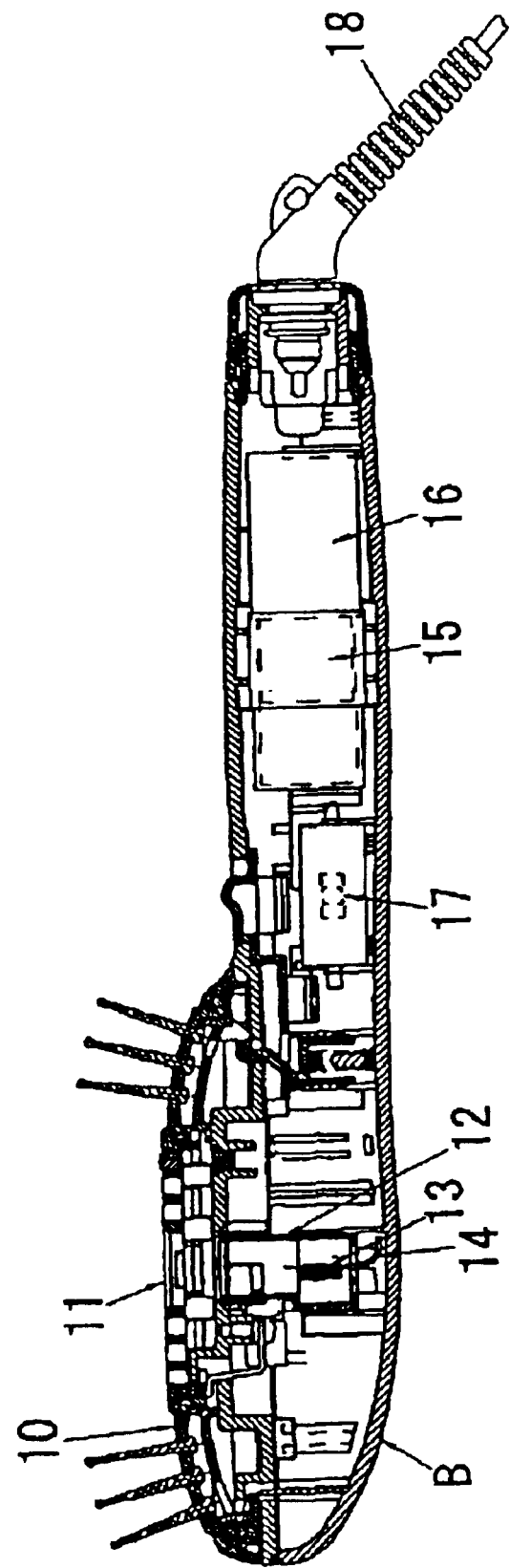
FIG. 14 is a sectional view of a conventional treatment apparatus.
Figure 15:
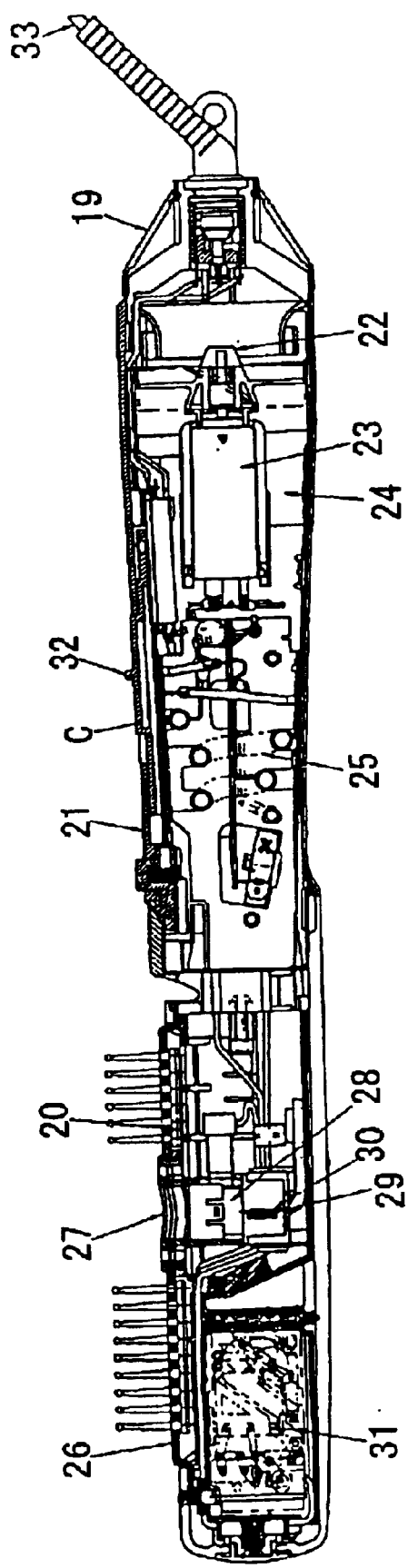
FIG. 15 is a sectional view of a conventional dryer.

FIGS. 12(a) and 12(b) show another example of a hair care apparatus, which is a brush with hair dryer function equipped with an air discharge outlet, an ion discharge outlet, a bristle. The apparatus includes a cylindrical housing 129, a suction inlet 127, an air discharge outlet 128, a fan 130 for blowing, a motor 131, flow controlling wings 132, and a heater 133. The cylindrical housing 129 also functions as a handle 7. The air discharge outlet 128 is formed on the bristle surface 134. Further, a steam discharge outlet 135 for discharging steam and an ion discharge outlet 136 for discharging negatively ionized air is also formed on the bristle surface 134. An ion nozzle 137 is connected to the ion discharge outlet 136. The ion nozzle 137 includes an ion electrode 130 which is connected to an ion generating circuit 140 via a high voltage lead wire 138. Negatively ionized air generated by the negative ion generator, which includes the ion electrode 139 and the ion generating circuit 140, is discharged from the ion discharge outlet 136. The steam discharge outlet 135 is also connected to the chamber 142 which contains a heater 141. Water is supplied to the heater 141 through capillary tubes formed in the felt 144 provided in the removable tank 143. A heater 141, the ion generating circuit 140, a motor, a heater 133, and power cord 151 to supply power are connected to a changeover switch 150 which is configured to control blowing, steam and negatively ionized air.

This brash having a dryer function can blow out warm or cold wind from the air discharge outlet 128 by driving fan 130 and by supplying power to the heater when necessary, and the hair is combed with the bristle 134 by holding the handle. Thus, arranging hair is possible while drying the hair. In operation, steam generated in the chamber 142 of the steam generating device can be discharged from the steam discharge outlet 135, while negatively ionized air generated in the negative ion generator is simultaneously discharged. One brash with dryer function can perform moisture retention, drying, setting of the hair, and irradiation of negatively ionized air, making better touch of the hear after hair care.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A skin care apparatus comprising:
    a skin care unit configured to perform skin care on a skin surface of human being and including a steam supplier configured to discharge steam toward the skin surface;
    an electric discharging device configured to discharge electricity to make the steam into fine particles; and
    a negative ion supplying unit configured to discharge negatively ionized air toward the skin surface and including a negative ion generator which is configured to generate the negatively ionized air.

2. A skin care apparatus according to claim 1, wherein said steam supplier comprises a steam nozzle from which the steam is configured to be discharged, and wherein said negative ion supplying unit comprises an ion nozzle from which the negatively ionized air is configured to be discharged and which is provided such that a steam discharge direction of the steam from the steam nozzle and an ion discharge direction of the negatively ionized air from the ion nozzle are substantially in parallel.

3. A skin care apparatus according to claim 2, wherein said steam nozzle and said ion nozzle are provided to be integrated such that the steam discharge direction and the ion discharge direction are adjustable.

4. A skin care apparatus according to claim 2, wherein said ion nozzle is positioned above said steam nozzle.

5. A skin care apparatus according to claim 2, wherein said steam nozzle includes a steam discharge outlet and wherein said ion nozzle includes an ion discharge outlet which is provided in a forward position in the ion and steam discharge directions with respect to the steam discharge outlet.

6. A skin care apparatus according to claim 1, further comprising:
    an electric terminal configured to be touched by the human being to maintain the skin surface at positive electric potential.

7. A skin care apparatus according to claim 1, wherein said negative ion generator utilizes a corona discharge.

8. A skin care apparatus according to claim 7, wherein said negative ion generator comprises an electrode connected to ground and a needle-shaped electrode which is provided to face the electrode and to which high voltage is applied.

9. A skin care apparatus according to claim 8, wherein said electrode has a half cylindrical shape in which said needle-shaped electrode is positioned.

10. A skin care apparatus according to claim 1, wherein said negative ion supplying unit is configured to discharge the negatively ionized air toward the skin surface while said skin care unit performs skin care on the skin surface.

11. A skin care apparatus comprising:
    a skin care unit configured to perform skin care on a skin surface of human being and including a steam supplier configured to discharge steam toward the skin surface;
    an electric discharging device configured to discharge electricity to make the steam into fine particles; and
    negative ion discharging means for discharging negatively ionized air toward the skin surface.

12. A method for performing skin care, comprising:
    treating skin surface of human being; and
    discharging negatively ionized air toward the skin surface,
    wherein the treating step includes making steam into fine particles by discharging electricity and discharging the fine particles of the steam toward the skin surface.

13. A method according to claim 12, wherein the fine particles of the steam and the negatively ionized air are discharged substantially in parallel.

14. A method according to claim 12, further comprising: maintaining the skin surface at positive electric potential.

15. A method according to claim 12, wherein the treating step and the discharging step are performed simultaneously.

16. A method according to claim 12, wherein the treating step and the discharging step are performed independently.

17. A method for performing skin care, comprising:
    treating skin surface of human being; and
    discharging negatively ionized air toward the skin surface,
    wherein the treating step includes discharging ultrasonic waves toward the skin surface.

18. A method according to claim 17, further comprising: maintaining the skin surface at positive electric potential.

19. A method according to claim 17, wherein the treating step and the discharging step are performed simultaneously.

20. A method according to claim 17, wherein the treating step and the discharging step are performed independently.

21. A method for performing skin care, comprising:
    treating skin surface of human being; and discharging negatively ionized air toward the skin surface, wherein the treating step and the discharging step are performed independently and wherein the treating step includes discharging steam toward the skin surface.

22. A method according to claim 21, wherein the steam and the negatively ionized air are discharged substantially in parallel.

23. A method according to claim 21, further comprising:
making the steam to fine particles by discharging electricity.

24. A method according to claim 21, wherein the treating step includes discharging ultrasonic waves toward the skin surface.

25. A method according to claim 21, wherein the treating step includes thermally stimulating the skin surface.

26. A method according to claim 21, wherein the treating step includes vibrating the skin surface.

27. A method according to claim 21, further comprising:
maintaining the skin surface at positive electric potential.

* * * * *